(12) United States Patent
Aubeuf-Prieur et al.

(10) Patent No.: US 11,925,914 B2
(45) Date of Patent: Mar. 12, 2024

(54) PERFORMIC ACID PRODUCTION SYSTEMS AND METHODS

(71) Applicant: Kemira Oyj, Helsinki (FI)

(72) Inventors: Patricia Aubeuf-Prieur, Roquelaure (FR); Iris Porat, Mableton, GA (US); Marco Stammegna, Cleveland, OH (US); Sampsa Greus, Espoo (FI)

(73) Assignee: KEMIRA OYJ, Helsinki (FI)

( * ) Notice: Subject to any disclaimer, the term of this patent is extended or adjusted under 35 U.S.C. 154(b) by 341 days.

(21) Appl. No.: 17/196,357

(22) Filed: Mar. 9, 2021

(65) Prior Publication Data
US 2021/0275984 A1 Sep. 9, 2021

Related U.S. Application Data

(60) Provisional application No. 62/987,186, filed on Mar. 9, 2020.

(51) Int. Cl.
| | |
|---|---|
| *B01J 14/00* | (2006.01) |
| *B01J 19/00* | (2006.01) |
| *B01J 19/24* | (2006.01) |
| *B01J 27/02* | (2006.01) |
| *C07C 407/00* | (2006.01) |
| *C07C 409/24* | (2006.01) |

(52) U.S. Cl.
CPC ......... *B01J 19/0033* (2013.01); *B01J 14/00* (2013.01); *B01J 19/0013* (2013.01); *B01J 19/245* (2013.01); *B01J 27/02* (2013.01); *C07C 407/00* (2013.01); *C07C 409/24* (2013.01); *B01J 2219/0004* (2013.01); *B01J 2219/00099* (2013.01); *B01J 2219/00195* (2013.01); *B01J 2219/00229* (2013.01); *B01J 2219/00236* (2013.01)

(58) Field of Classification Search
None
See application file for complete search history.

(56) References Cited

U.S. PATENT DOCUMENTS

| | | | | |
|---|---|---|---|---|
| 2017/0064949 A1* | 3/2017 | Kraus | ................... | C07C 407/00 |
| 2020/0139339 A1* | 5/2020 | Ozasa | ...................... | B01J 19/24 |

FOREIGN PATENT DOCUMENTS

WO  WO-9420424 A1 * 9/1994 .............. C02F 1/722

* cited by examiner

*Primary Examiner* — Jennifer A Leung
(74) *Attorney, Agent, or Firm* — Eversheds Sutherland (US) LLP

(57) ABSTRACT

Systems for producing performic acid and methods for producing performic acid. The systems may include two or more reactor units, two or more servient programmable logic controllers, a control panel, and a master programmable logic controller. The system may modify the production of performic acid in at least one of the two or more reactor units upon and/or after the occurrence of a disruptive event in order to maintain a desired level of performic acid production and/or a desired level of disinfection.

38 Claims, 4 Drawing Sheets

PERFORMIC ACID PRODUCTION SYSTEMS AND METHODS

CROSS-REFERENCE TO RELATED APPLICATIONS

This application claims priority to U.S. Provisional Application No. 62/987,186, filed Mar. 9, 2020, which is incorporated herein by reference.

FIELD OF THE DISCLOSURE

This disclosure relates generally to performic acid production systems and to methods for producing performic acid and, in particular, relates to performic acid production systems having two or more reactor units configured to maintain a desired level of performic acid production upon and/or after the occurrence of a disruptive event.

BACKGROUND

Performic acid is commonly used for disinfecting water or aqueous solutions. For example, performic acid may be used for treating drain water, water used in horticulture, or any water in need of treatment. Performic acid is an effective disinfectant for harmful microorganisms, such as fungi, viruses, bacteria, yeasts, and algae, and degrades into harmless byproducts, including carbon dioxide, oxygen, and water.

Prior performic acid production systems typically combine acids and hydrogen peroxide in a reactor to produce performic acid. In production systems in which performic acid is produced in a coil-type reactor, a ramp-up time of at least 10 minutes, often at least 20 minutes, is usually required before any performic acid is produced. Thus, planned downtime, such as for maintenance, or unplanned downtime resulting from, e.g., reactor malfunction, could disrupt the production of performic acid for the entire duration of the downtime and/or for the ramp-up time necessary for switching to a second reactor. Such occurrences, whether planned or unplanned, may, therefore, result in a period of zero or reduced performic acid production. Systems in which multiple, redundant apparatuses are combined can also increase complexity and often require multiple precursor sources and multiple product outlets.

Performic acid production typically involves the mixing of one or more acids, such as formic acid, with hydrogen peroxide in a specific, constant ratio to produce performic acid. Performic acid may be used to treat water and aqueous solutions due at least in part, to its ease of production and harmless byproducts. However, because of its instability, performic acid usually is produced on-site as the need arises.

High throughput applications of performic acid include treatment of municipal water supply, treatment of water for industrial farming, and the like. In some situations, continuous and uninterrupted water treatment is needed, such as to treat municipal water supply during and after a storm, during and after an event attracting a large amount of people, or in periods in which the concentration of microorganisms in the water is heightened with or without a change in overall flow rate. In some situations, varying amounts of performic acid are needed, such as a greater amount immediately following heavy rain, a lesser amount after water levels have reduced or in periods of drought, or varying amounts in response to the natural fluctuation of moisture in waste water. Increasing the number of apparatuses responsible for producing performic acid may meet the demands of a high throughput application, but the individual failure rates of each apparatus still results in the possibility that there may be a period of zero performic acid production, to say nothing of the increased cost of adding additional apparatuses.

Thus, performic acid production systems having the ability to maintain a desired level of performic acid production when a disruptive event occurs, and/or the ability to dynamically, in a relatively short period of time, change performic acid flow rate and/or concentration to react to production needs, would be beneficial.

BRIEF DESCRIPTION OF THE DRAWINGS

The detailed description is set forth with reference to the accompanying drawings. The use of the same reference numerals may indicate similar to identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

Figure 1:
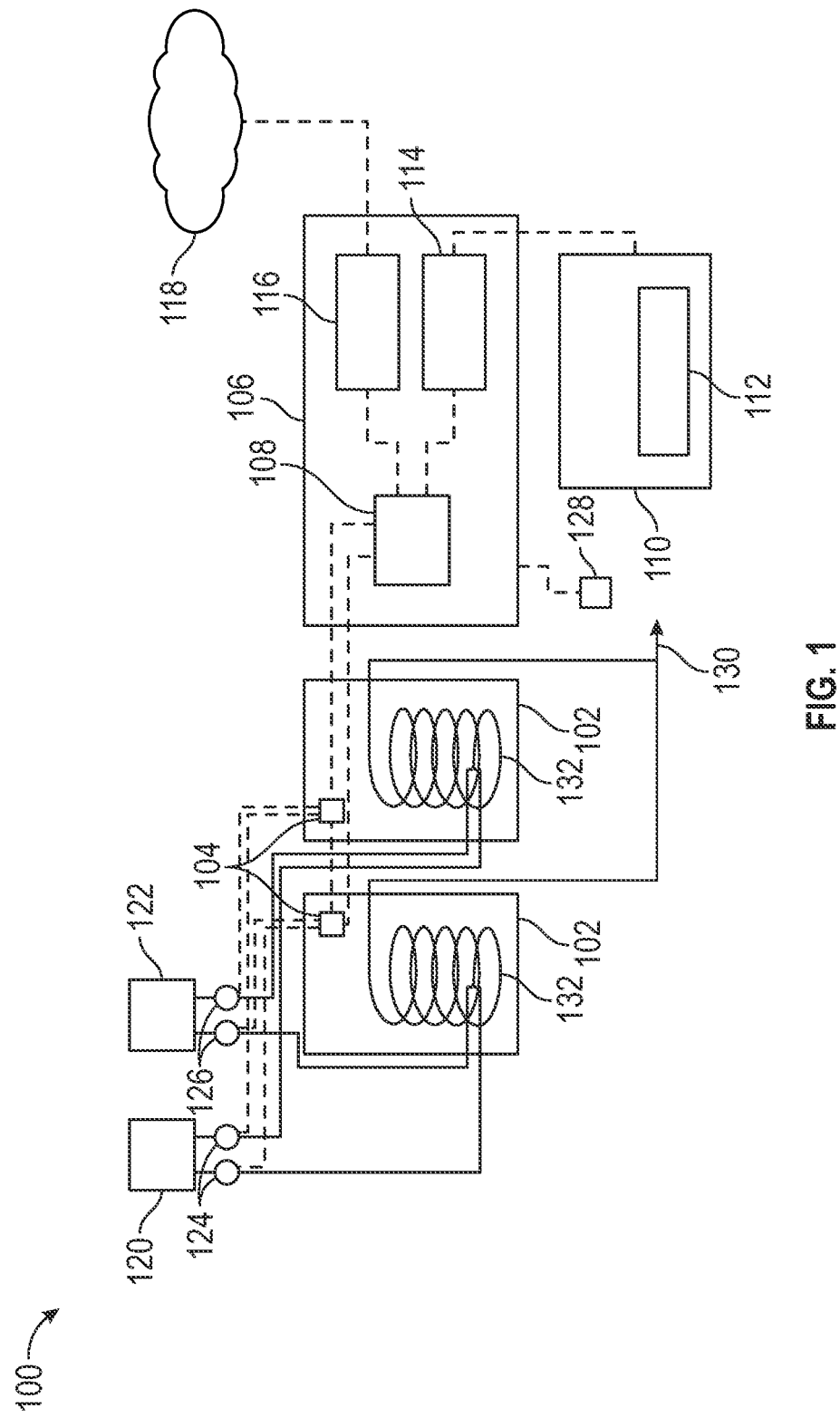
FIG. 1 is a schematic of an embodiment of a performic acid production system in accordance with the present disclosure.

Performic acid production systems and methods of producing performic acid are provided herein including performic acid production systems, and methods of production that advantageously reduce or eliminate the impact of reactor malfunction or downtime on performic acid production, increase the reliability of the system, increase the capabilities of the system to react to varying production demands, reduce the complexity of systems in which multiple means of production are combined, or a combination thereof. The present disclosure includes non-limiting embodiments of performic acid production systems. The embodiments are described in detail herein to enable one of ordinary skill in the art to practice the performic acid production systems and methods of producing performic acid, although it is to be understood that other embodiments may be utilized and that logical changes may be made without departing from the scope of the disclosure.

Throughout this disclosure, various aspects are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6, etc., as well as individual numbers within that range, for example, 1, 2, 3, 4, 5, and 6. This applies regardless of the breadth of the range.

Any known method of making performic acid can be used in the systems and methods herein. For example, performic acid may be produced by mixing 70-80 wt % formic acid and 30-50 wt % hydrogen peroxide, optionally in the presence of a catalyst. The catalyst may be combined with the formic acid to form a liquid containing, e.g., 70-80 wt % formic acid and 5-15 wt % catalyst, with the balance being water. Suitable catalysts may include sulfuric acid, nitric acid, hydrofluoric acid, phosphoric acid, a salt thereof, or a combination thereof. At equilibrium, a performic acid mixture may be produced containing performic acid, unreacted formic acid, unreacted hydrogen peroxide, and water. The concentration of performic acid in the performic acid mixture may be, e.g., from 10% to 16%, by weight, from 12% to 16%, by weight, from 7% to 12%, by weight, based on the weight of the performic acid mixture, or another concentration depending on the concentration of hydrogen peroxide used.

Performic acid production systems have been produced having multiple reactor units that may be controlled by separate programmable logic controllers that may themselves be controlled by a master programmable logic controller. By joining disparate reactor units by controls systems, embodiments of the systems can dynamically react to disruptive events, for example, by reducing the level of production that one reactor unit is responsible for while simultaneously increasing the level of production that one or more other reactor units is responsible for, thereby maintaining a desired level of performic acid production without any downtime for repairs or downtime for transferring responsibility from one apparatus to the next.

As used herein, a "disruptive event" refers to circumstances that disrupt the equilibrium operation of the system. As used herein, the "equilibrium operation" of the system refers to the average load of the system, i.e., the average flow of water to be treated, the average concentration of microorganisms, and/or the average number of active reactors and active reactor coils. In some instances, an increased flow rate of water to be treated resulting from heavy rainfall or a large gathering of people may disrupt the equilibrium operation of the system by requiring an increased flow rate of performic acid. In some instances, a heightened concentration of microorganisms, with or without an increased flow rate of water to be treated, may disrupt the equilibrium operation of the system by requiring an increased flow rate of performic acid, an increased concentration of performic acid, or both. In some instances, the planned or unplanned downtime of all or part of any single reactor unit may disrupt the equilibrium operation of the system by requiring another reactor unit to increase performic acid production. Any event that triggers a response in the system, i.e., that triggers the system to produce more or less performic acid and/or performic acid at a higher or lower concentration, is a "disruptive event."

Embodiments of the systems include reactor units, each having one or more coils kept in an isothermic state by a means for regulating temperature. Precursors may enter a coil at one end and react as they traverse the coil to produce performic acid prior to exiting the other end of the coil. Embodiments of the systems permit selection of (i) a coil volume, (ii) a coil length, (iii) a coil diameter, (iv) a flow rate of precursors, or (v) a combination thereof to determine the residence time of the precursors in the coil and, as a consequence, the concentration of performic acid that is produced.

Systems for Performic Acid Production

Systems for performic acid production are disclosed herein. In some embodiments, the system for producing performic acid includes two or more reactor units. Each of the reactor units may be in communication with a servient programmable logic controller (sPLC) such that each of two or more sPLCs is in communication with a different reactor unit. The system may include a control panel having a master programmable logic controller (mPLC) that is in communication with the sPLCs. In some embodiments, the system includes an automation unit that is in communication with the mPLC. The automation unit may have a user interface through which a user monitors and/or controls the system.

In some embodiments, the mPLC, at least one of the sPLCs, and/or at least one of the reactor units are configured to maintain a desired level of performic acid production upon and/or after the occurrence of a disruptive event.

As used herein, a "reactor unit" refers to any discrete unit in which performic acid is produced. The reactor unit may be a reactor, an apparatus including a reactor, or the like. The reactor unit may include one or more of a stirring element, a heating element, an agitation element, or the like. The reactor unit may be made out of any suitable material, such as stainless steel. The reactor unit may have any suitable volume depending on the application, and it may have any suitable shape.

In some embodiments, a "reactor unit" includes one or more coils disposed in a water bath. A coil is "disposed in a water bath" when it is arranged at a position that permits, or would permit, all or a portion of the coil to be submerged during normal operation of the water bath. The water bath may allow control over temperature, e.g., the temperature of the reactants or product while in a coil, upon exiting a coil, etc. The one or more coils may have a volume that determines, at least in part, the residence time of the precursors in the coil. The one or more coils may have a length that determines, at least in part, the residence time of the precursors in the coil. The flow rate of the precursors through the coil may determine, at least in part, the residence time of the precursors in the coil. Therefore, modifying (i) the volume of the coil (e.g., by switching a flow of reactants from a first coil to a second coil of a different volume, as described herein), (ii) the length of the coil (e.g., by switching a flow of reactants from a first coil to a second coil of a different length, as described herein), (iii) the diameter of the coil (e.g., by switching a flow of reactants from a first coil to a second coil of a different diameter, as described herein), (iv) the flow rate of precursors through a coil, (v) the temperature of the system, such as through a water bath having heating and/or cooling elements, or (vi) a combination thereof may determine, at least in part, the dosage of the performic acid produced. In some embodiments, a reactor unit has two coils that have different volumes, different lengths, and/or different diameters so that one unit is capable of producing two different concentrations of performic acid depending on the needs of the application. For example, a first coil having a first volume, first length, and a first diameter may be configured to produce a first concentration of performic acid in periods of average demand, while a second coil having a second, and greater, volume, a second, and greater, length, and/or a second, and greater, diameter may be configured to produce a second concentration of performic acid in periods of high demand. The first coil may be configured such that the precursors have a residence time of, e.g., 30 minutes, which correlates to a lower flow rate of water to be treated. The second coil may be configured such that the precursors have a residence time of, e.g., 10 minutes, which correlates to a higher flow rate of water to be treated. In some embodiments, a reactor unit includes a plurality of coils, each having a coil volume that is greater than, equal to, or less than any other coil volume. In some embodiments, a reactor unit includes a plurality of coils, each having a coil length that is greater than, equal to, or less than any other coil length. For example, a reactor unit may have three coils that have different volumes and/or different lengths so that one unit is capable of producing three different concentrations or dosages of performic acid depending on the needs of the application. In some embodiments, a reactor unit has four coils, five coils, six coils, or more than six coils, depending on the needs of the application. In some embodiments, the reactor unit includes a stirring element, heating element, cooling element, or a combination thereof. In some embodiments, the reactor unit includes a water buffer tank for circulating the water in the water bath and for flushing the coil(s) before, in between, or after performic acid production in a given coil.

As used herein, the "volume" of a coil refers to the length of the coil multiplied by the cross-sectional area of the coil. Since the residence time of precursors in the coil influences the concentration of performic acid produced, and since the volume of the coil influences the residence time of precursors in the coil, changing the volume of the coil or changing from a coil having a first volume to a coil having a second volume will result in performic acid of a different concentration being produced. Since the volume of the coil is related to both the length and the diameter of the coil, any instance of changing a "volume" or changing to a coil having a different "volume" in an effort to change the concentration of performic acid produced as described herein is therefore interchangeable with changing a "length" or changing to a coil having a different "length."

As used herein, a "programmable logic controller" refers to any computerized controller capable of sending and receiving communications from other programmable logic controllers, sensors such as thermocouples and actuators, and the like.

As used herein, an "automation unit" refers to a computer or other device capable of running programmed instructions designed to automate the system for producing performing acid. Any suitable computer or other device may be used.

In some embodiments, the mPLC is configured to receive a first instruction from the automation unit directing the system to produce a desired level of performic acid. The mPLC may be further configured to receive a status of each of the two or more reactor units from the sPLCs. Based on the desired level of performic acid production and the status of the reactor units, the mPLC may be further configured to send a second instruction to the sPLCs corresponding to a modified fraction of the desired level of performic acid. The sPLCs may be configured to modify the amount of performic acid produced by at least one of the reactor units based on the second instruction. In this way, the combined performic acid production from the reactor units may equal the desired level of performic acid production.

In other words, a disruptive event in one reactor unit may result in a status communicated by a sPLC to the mPLC. The mPLC may be configured to subsequently generate a second instruction to the sPLCs to modify the production of performic acid in the reactor units such that the combined performic acid production is equal to the desired level of performic acid production, despite the disruptive event in one reactor unit.

As used herein, "equal" to the desired level of performic acid production means within ±5% of the desired level of performic acid production.

As used herein, a "desired level of performic acid" refers to the amount and/or concentration of performic acid to be produced by the system. The amount may be in terms of a rate of production, such as in cubic meters per hour, and the desired level, therefore, may refer to a flow rate of a fluid that includes a concentration of performic acid. The amount may be in terms of a total volume of production, such as in L or tons. The concentration may be in terms of the parts per million (ppm) of performic acid in a fluid processed through a system. The desired level further refers to the set-point of the system, and may be changed by a user through the user interface on the automation unit. In response to increased or decreased demands for disinfection, a user may adjust the amount of performic acid produced, the rate of production of performic acid, the concentration of performic acid produced, or a combination thereof. The rate of production, concentration, and amount of performic acid produced is sometimes referred to as the "dosage" of performic acid.

The systems provided herein may be configured to have any production capacity. The production capacity, for example, may depend on a number of factors, such as a system's configuration, the number of reactor units, the number of operational v. standby reactor units, flow rate of fluid through a system or reactor unit, etc. In some embodiments, the systems provided herein have an average daily fluid flow rate of about 2 $m^3/s$ to about 12 $m^3/s$, about 3 $m^3/s$ to about 11 $m^3/s$, about 4 $m^3/s$ to about 11 $m^3/s$, about 4 $m^3/s$ to about 10 $m^3/s$, about 5 $m^3/s$ to about 9 $m^3/s$, about 5 $m^3/s$ to about 8 $m^3/s$, about 5 $m^3/s$ to about 7 $m^3/s$, about 5 $m^3/s$ to about 6 $m^3/s$, or about 5 $m^3/s$. In some embodiments, the systems provided herein produce performic acid at a concentration in the fluids flowing through a system or reactor unit of about 1 ppm to about 10 ppm, about 1 ppm to about 8 ppm, about 1 ppm to about 7 ppm, about 1 ppm to about 6 ppm, about 2 ppm to about 6 ppm, or about 3 ppm to about 6 ppm.

In some embodiments, the system includes a first source configured to supply hydrogen peroxide to each of the reactors units, and a second source configured to supply one or more acids to each of the reactor units. In this way, there may be a single source for supplying hydrogen peroxide to the two or more reactor units, and a single source for supplying one or more acids to the two or more reactor units, regardless of the number of reactor units. In some embodiments, the systems include more than one source configured to supply hydrogen peroxide, and/or more than one source configured to supply one or more acids. Each reactor unit, for example, may be in communication with a different source of hydrogen peroxide and/or one or more acids.

As used herein, a "source" refers to any reservoir and/or input of a precursor into the system. The source may refer to a reservoir such as a container, vat, barrel, or the like. The source may refer to an input, such as a valve, tube, channel, pipe, or the like. The source may refer to a reservoir and an input, such as a vat having a pipe directing a precursor into the system. The source may refer to an apparatus for supplying a precursor, such as a tank having auxiliary components including control valves, climate control, thermocouples, control systems, safety systems, and the like.

The one or more acids described herein, such as the one or more acids supplied to a reactor unit in the methods described herein, may include (i) at least one precursor acid, or (ii) at least one precursor acid and at least one catalyst. As used herein, "precursor acid" refers to an acid, such as formic acid, that is a reactant in a performic acid process. As used herein, "mixed acids" refers to a mixture of one or more precursor acids, such as formic acid, and one or more catalysts, such as sulfuric acid. Other suitable catalysts may include nitric acid, hydrofluoric acid, phosphoric acid, sulfuric acid, or a salt thereof.

In some embodiments, the system includes two or more hydrogen peroxide pumps in communication with the sPLCs. Each of the hydrogen peroxide pumps may be configured to control the flow rate of hydrogen peroxide from a first source to one of the reactor units. In some embodiments, the system includes two or more acid pumps in communication with the sPLCs. Each of the acid pumps may be configured to control the flow rate of acid from a second source to one of the reactor units. There may be one hydrogen peroxide pump and one acid pump for each reactor unit, or there may be more than one hydrogen peroxide pump and more than one acid pump for each reactor unit.

In some embodiments, each of the sPLCs is configured to send a third instruction to the hydrogen peroxide pumps and acid pumps based on the second instruction from the mPLC. The third instruction may include a modified flow rate to be achieved by the hydrogen peroxide pumps and the acid pumps. In other words, the sPLCs may be configured to modify the performic acid production in one of more of the reactor units by modifying the flow rate of hydrogen peroxide and acid to the reactor units based on the status of the reactor units and the desired level of performic acid production.

In some embodiments, the control panel includes a communications coupler in communication with the mPLC and the automation unit. In some embodiments, the communications coupler employs a PROFINET® communication protocol. In other embodiments, the communications coupler employs a PROFIBUS®DP communication protocol. In other embodiments, the communications coupler employs a MODBUS® TCP communication protocol. The communications coupler may transmit data from the automation unit to the mPLC relating to, e.g., the desired level of performic acid production, and the communications coupler may transmit data from the mPLC to the automation unit relating to, e.g., the status of the reactor units.

In some embodiments, the control panel includes a modem in communication with the mPLC. The modem may facilitate connecting the system to the internet and may connect the system to the internet through a virtual private network (VPN). In some embodiments, the system includes a cloud-based software platform in communication with the modem. The cloud-based software platform may be configured to facilitate quality control and/or maintenance of the reactor units. In other words, when a reactor unit experiences a disruptive event, the sPLC may communicate the status of the reactor unit to the mPLC, and the mPLC may communication the reactor unit status through the modem to the cloud-based software platform so that support can be provided by, e.g., the system manufacturer, a troubleshooting contractor, or the like.

In some embodiments, the system has at least one standby reactor unit configured to produce zero or a nominal amount of performic acid prior to the occurrence of the disruptive event. In other words, the system may have a standby reactor unit configured to produce performic acid only in the event of a disruptive event to one or more other reactor units. For example, prior to the occurrence of a disruptive event, a system having three reactor units may have two reactor units each producing 50% of the desired level of performic acid and one reactor unit producing 0% of the desired level of performic acid.

As used herein, a "standby" reactor unit is a reactor unit that produces zero or a nominal amount of performic acid prior to the occurrence of a disruptive event. As described previously, when a reactor unit includes a coil, a ramp-up time is required (which includes the time needed for precursors to travel through at least part of the coil) before the reactor unit is capable of producing performic acid. Thus, in some embodiments, a "standby" reactor may produce zero performic acid, and is used in the event of a planned disruptive event that does not require an immediate switch to the standby reactor. In other embodiments, the "standby" reactor may produce a nominal amount of performic acid, thereby eliminating the need for a period of ramp-up, and the standby reactor is used when an unplanned disruptive event necessitates an immediate switch the standby reactor. As used herein, a "nominal amount" of performic acid is an amount equal to or less than 10% of the maximum performic acid production capacity of a particular reactor, and a "non-nominal amount" of performic acid is an amount greater than 10% of the performic acid production capacity of a particular reactor. The production capacity may be any of those described herein (e.g., concentration of performic acid produced, amount of performic acid product per a unit of time, etc.).

In other embodiments, each of the reactor units is configured to produce a fraction of the desired level of performic acid prior to the occurrence of the disruptive event. In other words, each reactor unit may be configured to contribute to the overall production of performic acid. For example, prior to the occurrence of a disruptive event, a system having three reactor units may have one reactor responsible for 50% of the desired level of performic acid, and two reactors each responsible for 25% of the desired level of performic acid.

In some embodiments, the system includes one or more uninterruptible power supplies (UPSs) in communication with (i) the control panel, (ii) the two or more reactor units (iii) the two or more sPLCs, (iv) or a combination thereof to ensure constant supply of power. In some embodiments, a PLC in communication with control panel will also supply power to the reactor units and/or sPLCs by virtue of their connection to the control panel.

In some embodiments, the system includes a product outlet configured to accept a product including performic acid. For example, there may be a single product outlet configured to accept the performic acid produced by all reactor units, which may reduce the complexity and interchangeability of the system and reactor units. As a further example, a system may include two or more product outlets.

In some embodiments, the system is configured to maintain a desired level of performic acid production when a disruptive event occurs. A "disruptive event" may include any planned or unplanned incident that requires the systems to act as described herein in order to maintain a desired level of performic acid production. For example, a disruptive event may include a failure of at least one of the two or more reactor units. In other embodiments, the disruptive event includes scheduled maintenance of a reactor unit, replacement of a reactor unit, maintenance of auxiliary components, or the like.

FIG. 1 is a schematic of an embodiment of a system 100 for producing performic acid including reactor units 102. Each reactor unit 102 is associated with a servient programmable logic controller (sPLC) 104. The system 100 includes a control panel 106 that includes a master programmable logic controller (mPLC) 108. The mPLC 108 is in communication with the sPLCs 104 and an automation unit 110 having a user interface 112. The mPLC 108 communicates with the automation unit 110 through a communications coupler 114. A modem 116 is in communication with the mPLC 108 and transmits information to a cloud-based software platform 118. A first source 120 supplies hydrogen peroxide to a coil 132 in each reactor unit 102, and a second source 122 supplies acid to the coil 132 in each reactor unit 102. The flow rate of hydrogen peroxide is controlled by hydrogen peroxide pumps 124, and the flow rate of acid is controlled by acid pumps 126. The system 100 includes an uninterruptible power supply (UPS) 128 in communication with the control panel 106. The system 100 includes product outlet 130 configured to accept a product including performic acid from each of the reactor units 102.

In some instances, there are two reactor units. In other instances, there are three reactor units. In other instances, there may be four, five, six, or more than six reactor units. Any suitable number of reactor units may be used in the system depending on the needs of the system and factors such as reactor unit failure rate, reactor unit size, desired throughput, acceptable limits of reactor unit production, desired number of standby units, and the like.

In some instances, each reactor unit is in communication with a disparate sPLC. In other instances, the two or more sPLCs are subcomponents in a unitary device, each sPLC in communication with a reactor unit. For example, each sPLC may be a discrete computer in communication with a reactor unit, or there may be a server bank having multiple discrete server processors operating as the sPLCs that are each in communication with a reactor unit. The decision to describe two or more disparate sPLCs is in the interest of brevity only, and any suitable configuration of sPLCs may be used. In some instances, each sPLC is located proximal to the reactor unit it controls. In other instances, each sPLC is located remote to the reactor unit it controls.

In some instances, the mPLC, modem, and communications coupler may be disparate components associated with the control panel, or they may be components in a single unit, such as a computer. The automation unit may be separate from the control panel, or it may be joined with the control panel, the mPLC, modem, and communications coupler to form a unitary device. Any of the components may be joined together so that there may be one, two, three, or more than three components in the form of, e.g., computers that are configured to communicate with each other as described herein.

In some instances, the cloud-based software platform is located remote to the system such that it communicates with the system over, e.g., the internet. In other instances, the software platform is located both local to the system in the form of, e.g., a locally-installed software program, and remote to the system in the form of, e.g., a remote software such that the locally-installed software program and remote software communicate with each other. Any suitable configuration may be used for the cloud-based software program such that maintenance and support may be provided upon and/or after the occurrence of a disruptive event.

In some instances, the hydrogen peroxide pumps may be located proximal to the first source and remote from the reactor units. In other instances, each hydrogen peroxide pump may be located proximal to the reactor unit it supplies. Similarly, the acid pumps may be located proximal to the second source and remote from the reactor units, or each acid pump may be located proximal to the reactor unit it supplies.

Figure 2:
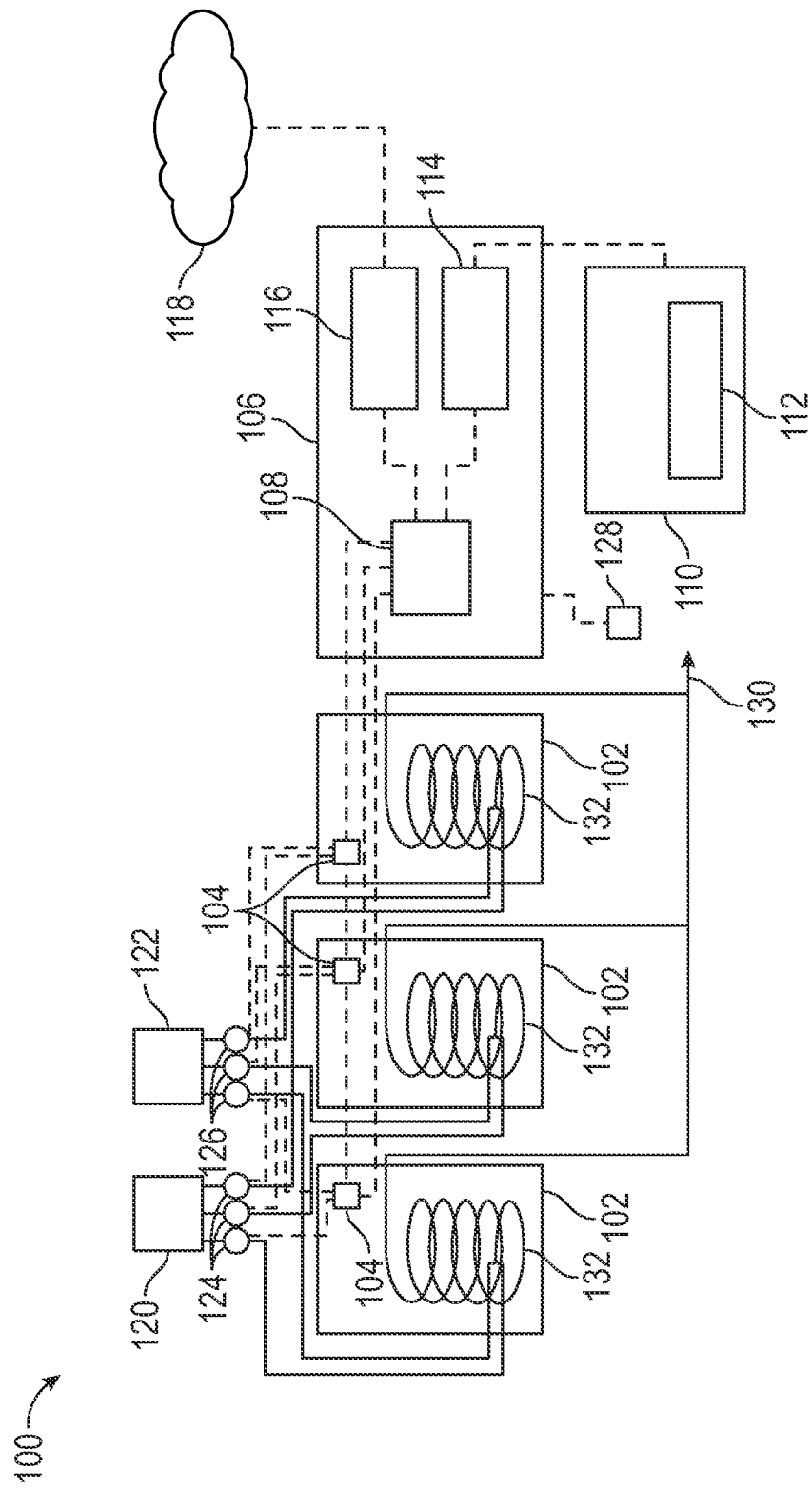
FIG. 2 is a schematic of an embodiment of a performic acid production system in accordance with the present disclosure.

FIG. 2 is a schematic of an alternative embodiment of a system 200 for producing performic acid illustrating three reactor units 102 with corresponding sPLCs 104, hydrogen peroxide pumps 124, acid pumps 126, and coils 132. Thus, it is to be understood that the systems described herein may scale up to any number of reactor units through the addition of the necessary components, while maintaining a single first source 120, a single second source 122, a single product outlet 130, a single automation unit 110, and a single control panel 106 having a mPLC 108, a modem 116, and a coupler 114.

Figure 3:
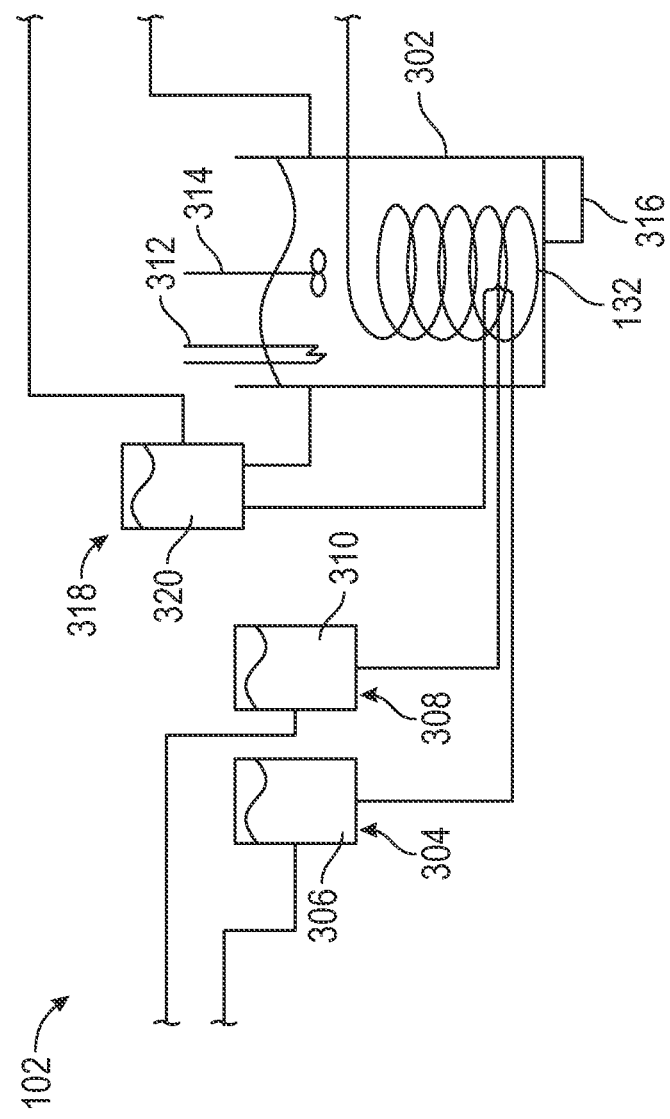
FIG. 3 is a schematic of an embodiment of a reactor unit in accordance with the present disclosure.

FIG. 3 is a schematic of an embodiment of a reactor unit 102 having coil 132 and water bath 302. A first buffer tank 304 is configured to store hydrogen peroxide 306 supplied by the first source (not pictured), and a second buffer tank 308 is configured to store acids 310 supplied by the second source (not pictured). Heating element 312 is configured to maintain a desired temperature in the water bath 302, stirring element 314 is configured to circulate the water in the water bath 302, and cooling element 316 is configured to cool the water bath. A water buffer tank 318 is configured to store water 320 supplied by a water source (not pictured), and supply the water to the water bath 302. The water 320 in the buffer tank 318 is further configured to flush coil 132 before or after performic acid production, or in between performic acid production cycles. The water 320 in the buffer tank 318 may be supplied to the water bath 302 and/or the coil 132 by a pump, by gravity, or through another suitable means for supplying water 320.

Figure 4:
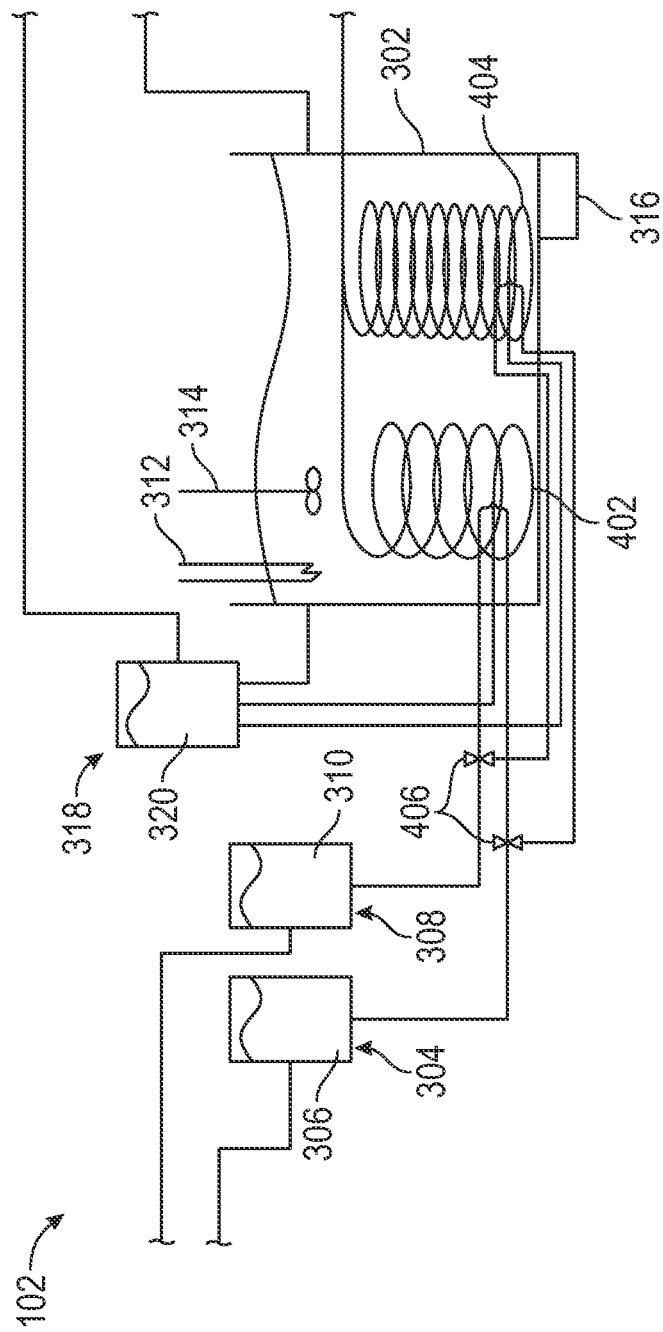
FIG. 4 is a schematic of an embodiment of a reactor unit in accordance with the present disclosure.

FIG. 4 is a schematic of an embodiment of a reactor unit 102 having a first coil 402 having a first length, and a second coil 404 having a second length. The first length and the second lengths are different such that the volume of the first coil and the volume of the second coil are different, and the residence time of the precursors in each coil are similarly different. First coil 402 and second coil 404 may also have different diameters. In this way, performic acid of two different flow rates may be produced by a single reactor unit 102, correlating to two different dosages of performic acid. Coil valves 406 are configured to control which of coils 402, 404 are used for the production of performic acid. In some instances, the coil valves redirect the flow of precursors from one coil to another coil, simultaneously providing precursors to one coil while ceasing the flow of precursors to another coil. In some instances, the valves start or stop the flow of precursors to a particular coil, so that there is one valve for each precursor and for each coil. Any suitable configuration of a coil valve or a plurality of coil valves may be used to switch the flow of precursors from one coil to another coil.

In some instances, performic acid may require 10-30 minutes retention time in a particular coil. In circumstances in which the flow rate of water to be treated increases, the performic acid production increases accordingly. In systems without multiple coils and the control systems as described herein, the concentration of the performic acid in response to the increased flow rate of water to be treated may be inadequate to treat the water. In the systems and methods described herein, a coil of an increased volume, an increased length, and/or an increased diameter may be engaged to increase the residence time of precursors and therefore produce performic acid at an increased concentration while maintaining the increased flow rate necessary to treat the increased flow rate of water to be treated.

In some embodiments, pumps (not pictured) may be positioned in the outlet from each reactor, such as to further modify the dosage of performic acid produced by each reactor and/or by the overall system.

In some embodiments, the reactor unit depicted in FIG. 3 is used in the embodiments of systems depicted in FIG. 1 and FIG. 2. In some embodiments, the reactor unit depicted in FIG. 4 is used in the embodiments of systems depicted in FIG. 1 and FIG. 2. In some embodiments, the embodiments of systems depicted in FIG. 1 and FIG. 2 include reactor units resembling those depicted in FIG. 3 and FIG. 4. Thus, the reactor units depicted in the embodiments of the systems in FIG. 1 and FIG. 2 may each include multiple coils, such that a two-reactor system may have four, five, six, or more than six coils in total. Thus, the reactor units depicted in the embodiments of the systems in FIG. 1 and FIG. 2 may include buffer tanks for the precursors, a buffer tank for the water bath, heating elements, stirring elements, one or more coils, and/or valves for selecting coils.

In some instances, precursors enter a coil at an end arranged nearer the bottom of the water bath than a second end of the coil, and the precursors react to produce performic acid as they ascend through the coil to the second end, which is nearer the top of the water bath. In other instances, the direction of flow is reversed, with precursors travelling downward. In some instances, the coil is curled along a longitudinal axis that is parallel with the ground, so that precursors enter on the "left," and performic acid exits on the "right", or vice versa. Any suitable orientation of the coil may be used. In some instances, a coil has a circular cross-section when viewed at any point along its longitudinal axis. In other instances, a coil has a polygonal cross-section when viewed at any point along its longitudinal axis. The coil may include any "tube" or similar conduit having (i) an inlet and an outlet, and (ii) any shape that permits at least partial submersion in a water bath, as described herein, including shapes that feature one or more spirals (e.g., a spring shape, a "paperclip" shape), curves, a substantially elongated portion, any other feature, or a combination thereof. In some instances, the shape of the coil is limited by the size and dimensions of the water bath such that, e.g., the "coil" may be a substantially straight tube having a volume suitable for the production of performic acid, provided that the water bath has a size and dimensions corresponding to the size and shape of the coil.

In some instances, a reactor unit including two or more coils has one common water bath and each coil is disposed in the water bath. In other instances, each of the coils is disposed within a separate water bath, with each water bath being stirred by separate stirring elements, heated by separate heating elements, and/or cooled by separate cooling elements.

In some instances, a reactor unit including two or more coils has coils of varying volumes, varying lengths, and/or varying diameters, as previously described. In other instances, the coils have the same volume, same length, and same diameter. In some instances, a reactor unit includes one, two, three, four, or more than four coils. A reactor unit may include a plurality of coils, each with a different volume, a different length, and/or a different diameter suitable to producing performic acid at a specific dosage when supplied with a specific flow rate of precursors, thereby resulting in a corresponding number of different dosages at which performic acid may be produced. A reactor unit may include a plurality of coils, where two or more coils have the same volume, the same length, and the same diameter.

In some embodiments, a system including two reactor units may operate with both reactor units responsible for 50% of the desired level of performic acid. In other embodiments, one reactor unit may be initially responsible for a larger fraction of the desired level of performic acid while the other reactor unit may be initially responsible for a smaller fraction of the desired level of performic acid. In some embodiments having three or greater reactor units, each reactor unit may be responsible for an equivalent fraction of the desired level of performic acid. In other embodiments, each reactor unit may be responsible for a different fraction of the desired level of performic acid. Any suitable division of the responsibility for producing the desired level of performic acid may be used.

In some embodiments, one or more reactor units may be initially responsible for zero performic acid production. In other words, one or more reactor units may be standby reactors responsible only for producing performic acid when a disruptive event occurs.

In some embodiments, a reactor unit experiencing a disruptive event may have a modified fraction of the desired level of performic acid production that is greater than zero, but less than the initial fraction of the desired level. In other words, a reactor unit experiencing a disruptive event may merely reduce the level performic acid production, but not completely cease production. In other embodiments, a reactor unit experiencing a disruptive event may reduce production to zero, while the remaining reactor unit(s) increase production proportionally to ensure the desired level of performic acid is produced.

While the reactor units in FIG. 1 and FIG. 2 are depicted as having the same size, the reactor units may or may not be the same size. In some embodiments, two or more identical reactor units are used. In other embodiments, the reactor units have different sizes, different materials of construction, different auxiliary components such as stirrers, lids, agitators, or the like. Any suitable reactor unit(s) may be used alongside any other suitable reactor unit(s). The depiction of the specific reactor units in the Figures to the exclusion of other possible combinations that are contemplated herein is in the interest of brevity only.

Methods of Producing Performic Acid

Methods of producing performic acid are also disclosed herein. In one aspect, a method includes providing any one of the systems as described herein. In another aspect, a method includes providing two or more reactor units. In some embodiments, the method includes sending a first instruction from an automation unit having a user interface to a master programmable logic controller (mPLC). The method may include sending a status of the two or more reactor units from two or more servient programmable logic controllers (sPLCs) to the mPLC. The method may include sending a second instruction from the mPLC to the sPLCs corresponding to a modified fraction of the desired level of performic acid to be produced by the reactor units. The method may include modifying an amount of performic acid produced by the reactor units based on the second instruction. In some embodiments, the mPLC, sPLCs, and/or the reactors units maintain a desired level of performic acid production upon and/or after the occurrence of a disruptive event.

In some embodiments, the method includes supplying hydrogen peroxide from a first source to each of the reactor units. The method may include supplying acid from a second source to each of the reactor units. In some embodiments, the method includes controlling the flow rate of hydrogen peroxide from the first source to the reactor units using two or more hydrogen peroxide pumps. In some embodiments, the method includes controlling the flow rate of acid from the second source to the reactor units using two or more acid pumps.

In some embodiments, modifying the amount of performic acid produced by the reactor units includes sending a third instruction from the sPLCs to the hydrogen peroxide pumps and the acid pumps in response to the second instruction from the mPLC, wherein the third instruction includes a modified flow rate.

In some embodiments, the reactor units include one or more coils disposed within one or more water baths. In some embodiments, modifying the amount of performic acid produced by the reactor units includes sending a signal to a coil valve to switch from a first coil having a first volume, a first length, and a first diameter to a second coil having a second volume, a second length, and/or a second diameter as described herein. The first length may be different from the second length, and the length of the coil may determine, at least in part, the residence time of the precursors in the coil which, in turn, may determine, at least in part, the concentration of performic acid produced. The first volume may be different from the second volume, and the volume of the coil may determine, at least in part, the residence time of the precursors in the coil which, in turn, may determine, at least in part, the concentration of performic acid produced.

In some embodiments, the method includes sending the first instruction from the automation unit through a communications coupler to the mPLC. In some embodiments, the communications coupler employs a PROFINET® communication protocol. In other embodiments, the communications coupler employs a PROFIBUS®DP communication protocol. In other embodiments, the communications coupler employs a MODBUS® TCP communication protocol. The communications coupler may transmit data from the automation unit to the mPLC relating to, e.g., the desired level of performic acid production, and the communications coupler may transmit data from the mPLC to the automation unit relating to, e.g., the status of the reactor units.

In some embodiments, the method includes sending the status of the reactor units through a modem to a cloud-based software platform. The cloud-based software platform may facilitate quality control and/or maintenance of the reactor units in the event of a service need.

In some embodiments, modifying the amount of performic acid produced by the reactor units includes increasing the production of performic acid in a standby reactor from zero or a nominal amount to the modified fraction of the desired level of performic acid. In other embodiments, modifying the amount of performic acid produced by the reactor units includes modifying the production of performic acid in the reactor units from an initial fraction to the modified fraction of the desired level of performic acid.

In some embodiments, the method includes supplying power from one or more uninterruptible power supplies (UPSs) to the control panel, reactor units, and/or sPLCs in the event of a power failure.

In some embodiments, the method includes accepting a product including performic acid from each of the reactor units at a product outlet.

In another aspect, a method includes providing at least one reactor unit including a water bath and two or more coils disposed in the water bath. In some embodiments, the method includes sending a first instruction from an automation unit to a master programmable logic controller (mPLC). The method may include sending a status of the at least one reactor unit from at least one servient programmable logic controller (sPLC) to the mPLC. The method may include sending a second instruction from the mPLC to each of the at least one sPLCs corresponding to a desired level of performic acid production in each of the two or more coils. In some embodiments, the second instruction is generated in response to a disruptive event comprising (i) a demand for an increased flow rate of performic acid, (ii) a demand for an increased concentration of performic acid, (iii) a demand for a decreased flow rate of performic acid, (iv) a demand for a decreased concentration of performic acid, or (v) a combination thereof.

In some embodiments, the method includes supplying hydrogen peroxide from a first source to the at least one reactor unit. The method may include supplying acid from a second source to the at least one reactor unit. In some embodiments, the method includes controlling the flow rate of hydrogen peroxide from the first source to the at least one reactor unit using one or more acid pumps. In some embodiments, the method includes controlling the flow rate of acid from the second source to the at least one reactor unit using one or more acid pumps.

In some embodiments, modifying the amount of performic acid produced by the at least one reactor unit includes sending a third instruction from the at least one sPLCs to the at least one hydrogen peroxide pump and the at least once acid pump in response to the second instruction from the mPLC, wherein the third instruction includes a modified flow rate.

In some embodiments, modifying the amount of performic acid produced by the at least one reactor unit includes sending a signal to a coil valve to switch from a first coil having a first volume to a second coil having a second volume as described herein. In some embodiments, modifying the amount of performic acid produced by the at least one reactor unit includes sending a signal to a coil valve to switch from a first coil having a first length to a second coil having a second length as described herein. The first length may be different from the second length, and the length of the coil may determine, at least in part, the residence time of the precursors in the coil which, in turn, may determine, at least in part, the concentration of performic acid produced. The first volume may be different from the second volume, and the volume of the coil may determine, at least in part, the residence time of the precursors in the coil which, in turn, may determine, at least in part, the concentration of performic acid produced.

EXAMPLE

An embodiment of a system for producing performic acid was produced. The system of this example had four reactor units. The system was supplied by two 28 $m^3$ storage tanks containing hydrogen peroxide (50 wt % in water) and two 28 $m^3$ storage tanks containing a mixture of formic acid and sulfuric acid. Two reactor units were used to produce performic acid, while two reactor units were initially kept on standby. The hydrogen peroxide pumps and acid pumps supplied precursors at a rate of 200 L/h.

The system of this example performed according to the following parameters:

| Operation | Maximum Flow ($m^3$/h) | Average Flow ($m^3$/h) | Performic Acid (ppm) |
|---|---|---|---|
| Two Reactor Units at Maximum Capacity | 38,023 | 19,309 | 3.3 (Maximum Flow) 6.5 (Average Flow) |
| One Reactor Unit at Maximum Capacity | 38,023 | 19,309 | 1.65 (Maximum Flow) 3.25 (Average Flow) |

This system was capable of tolerating two disruptive events, i.e., two reactor units could (i) be taken offline or (ii)

malfunction, without impacting performance. A third disruptive event to a third reactor unit could result in one unit at maximum capacity capable of producing 1.65 ppm of performic acid at a maximum flow rate of 38,023 m$^3$/h, or 3.25 ppm of performic acid at an average flow rate of 19,309 m$^3$/h.

Thus, by controlling the flow rate of precursors, the volume of the coil in a reactor unit, the length of the coil in a reactor unit, or a combination of the flow rate of precursors, the volume of the coil, and the length of the coil simultaneously, the concentration or dosage of performic acid produced could be controlled. In situations in which a lower concentration of performic acid was desired, the needs could be met with a smaller volume coil, a smaller length coil, and/or an increased flow rate of precursors. Similarly, in situations in which a higher concentration of performic acid was desired, the needs could be met with a larger volume coil, a larger length coil, and/or a lower flow rate of precursors. Due to the ability to modify the flow rate of precursors, the length of the coil, and the diameter of the coil, a wide range of performic acid concentrations may be achieved, dramatically increasing flexibility of the performic acid production system without the need to costly downtime and ramp-up of secondary units.

In this example, the storage tanks were housed in shipping containers having dimensions of 2.6 m×2.4 m×12.2 m. The shipping containers were climate controlled and included modems for connection with a cloud-based software platform for monitoring and support service. Each storage tank included a bund for secondary containment of the entire tank volume in the event of a tank failure. Since the tank was stored in a shipping container, the fumes from such a tank failure were also be contained. Each container included instruments for measuring precursor volume and temperature, with alarms to warn of low level and low/high temperature. Each source of acid included formic acid vapor detection.

Systems for producing performic acid and associated methods have been provided. These systems include two or more reactor units controlled by two or more servient programmable logic controllers, and a control panel having a master programmable logic controller. In some embodiments, the system is configured to modify the level of production of performic acid in at least one of the two or more reactor units upon and/or after a disruptive event.

While the disclosure has been described with reference to a number of embodiments, it will be understood by those skilled in the art that the disclosure is not limited to such disclosed embodiments. Rather, the disclosure can be modified to incorporate any number of variations, alterations, substitutions, or equivalent arrangements not described herein, but which are commensurate with the spirit and scope of the disclosure. Conditional language used herein, such as "can," "could," "might," or "may," unless specifically stated otherwise, or otherwise understood within the context as used, generally is intended to convey that certain embodiments include, while other embodiments do not include, certain features, elements or functional capabilities. Additionally, while various embodiments of the disclosure have been described, it is to be understood that aspects of the disclosure may include only some of the described embodiments. Accordingly, the disclosure is not to be seen as limited by the foregoing description, but is only limited by the scope of the appended claims.

The invention claimed is:

1. A system for producing performic acid, the system comprising:
   two or more reactor units, wherein at least one reactor unit of the two or more reactor units comprises a water bath and one or more coils disposed in the water bath;
   two or more servient programmable logic controllers (sPLCs), wherein each of the two or more sPLCs is in communication with a different reactor unit of the two or more reactor units;
   a control panel comprising a master programmable logic controller (mPLC) in communication with the two or more sPLCs; and
   an automation unit having a user interface, wherein the automation unit is in communication with the mPLC;
   wherein (i) the mPLC, (ii) at least one of the two or more sPLCs, and (iii) at least one of the two or more reactor units, are configured to maintain a desired level of performic acid production upon and/or after the occurrence of a disruptive event, and
   wherein the two or more sPLCs are configured to detect the disruptive event and communicate a status of the two or more reactor units to the mPLC.

2. The system of claim 1, wherein:
   the mPLC is configured to receive from the automation unit a first instruction comprising the desired level of performic acid production,
   the mPLC is configured to receive a status of the two or more reactor units from each of the two or more sPLCs,
   the mPLC is configured to send a second instruction, based on the desired level of performic acid production and the status of the two or more reactor units, to each of the two or more sPLCs upon and/or after the occurrence of the disruptive event, the second instruction comprising a modified fraction of the desired level of performic acid production, and
   the sPLCs are configured to modify, based on the second instruction, an amount of performic acid produced by at least one of the two or more reactor units, such that a combined performic acid production of the two or more reactor units equals the desired level of performic acid production.

3. The system of claim 1, wherein at least one of the two or more reactor units comprises two coils and at least one coil valve,
   wherein a first coil having a first volume is configured to produce a first concentration of performic acid,
   wherein a second coil having a second volume is configured to produce a second concentration of performic acid, wherein the second concentration is greater than the first concentration,
   wherein the second volume is different than the first volume, and
   wherein the at least one coil valve is configured to shift a supply of performic acid precursors from the first coil to the second coil, or vice-versa.

4. The system of claim 1, wherein at least one of the two or more reactor units further comprises a plurality of coils and a plurality of coil valves,
   wherein each coil of the plurality of coils has a coil volume,
   wherein each coil volume is greater than, equal to, or lesser than every other coil volume,
   wherein each coil volume is configured to produce a concentration of performic acid, and
   wherein each coil valve of the plurality of coil valves is configured to shift a supply of performic acid precursors from one of the plurality of coils to a different one of the plurality of coils.

5. The system of claim 1, wherein each of the two or more reactor units further comprises (i) a stirring element, (ii) a heating element, (iii) a cooling element, (iv) a water buffer tank, or (v) a combination thereof.

6. The system of claim 2, further comprising:
a first source configured to supply hydrogen peroxide to each of the two or more reactor units; and
a second source configured to supply one or more acids to each of the two or more reactor units.

7. The system of claim 6, wherein the second source comprises one or more acids, the one or more acids comprising formic acid and a catalyst.

8. The system of claim 7, wherein the catalyst comprises sulfuric acid, nitric acid, hydrofluoric acid, phosphoric acid, a salt thereof, or a combination thereof.

9. The system of claim 6, wherein at least one of the two or more reactor units further comprises:
a first buffer tank configured to store hydrogen peroxide supplied by the first source,
a second buffer tank configured to store the one or more acids supplied by the second source.

10. The system of claim 6, further comprising:
two or more hydrogen peroxide pumps in communication with the two or more sPLCs, wherein each of the two or more hydrogen peroxide pumps is configured to control a flow rate of the hydrogen peroxide of the first source to at least one of the two or more reactor units; and
two or more acid pumps in communication with the two or more sPLCs, wherein each of the acid pumps is configured to control a flow rate of the one or more acids of the second source to at least one of the two or more reactor units.

11. The system of claim 10, wherein each of the two or more sPLCs is configured to send a third instruction to at least one of the two or more hydrogen peroxide pumps and to at least one of the two or more acid pumps in response to the second instruction from the mPLC, wherein the third instruction comprises a modified flow rate.

12. The system of claim 1, wherein the control panel further comprises a communications coupler in communication with the mPLC and the automation unit configured to employ a communication protocol.

13. The system of claim 1, wherein the control panel further comprises: a modem in communication with the mPLC; and
a cloud-based software platform in communication with the modem,
wherein, in response to receiving a status of at least one of the two or more reactor units from the mPLC, the cloud-based software platform is configured to facilitate (i) quality control, (ii) maintenance of the two or more reactor units, or (iii) a combination thereof in the event of a service need by coordinating support by a system manufacturer or a troubleshooting contractor.

14. The system of claim 1, wherein the system further comprises at least one standby reactor unit that produces zero performic acid prior to the occurrence of the disruptive event.

15. The system of claim 1, wherein the system further comprises at least one standby reactor unit that produces (i) a nominal level of performic acid prior to the occurrence of the disruptive event, and (ii) a non-nominal level of performic acid upon and/or after the occurrence of the disruptive event without a ramp-up period.

16. The system of claim 1, wherein each of the two or more reactor units contributes a fraction of the desired level of performic acid production prior to the occurrence of the disruptive event.

17. The system of claim 1, further comprising one or more uninterruptible power supplies (UPSs) in communication with (i) the control panel, (ii) the two or more reactor units, (iii) the two or more sPLCs, or (iv) a combination thereof.

18. The system of claim 1, further comprising a product outlet configured to accept a product comprising performic acid from each of the two or more reactor units.

19. The system of claim 1, wherein the disruptive event detected by the two or more sPLCs comprises (i) an unplanned failure of at least one of the two or more reactor units, (ii) a planned period of maintenance, (iii) a demand for an increased flow rate of performic acid, (iv) a demand for an increased concentration of performic acid, (v) a demand for a decreased flow rate of performic acid, (vi) a demand for a decreased concentration of performic acid, or (vii) a combination thereof.

20. A method for producing performic acid, the method comprising:
providing the system of claim 1;
sending a first instruction from the automation unit to the master programmable logic controller (mPLC);
supplying (i) hydrogen peroxide from a first source, and (ii) one or more acids from a second source to each of the two or more reactor units;
sending a status of each of the two or more reactor units from each of two or more servient programmable logic controllers (sPLCs) to the mPLC;
sending a second instruction from the mPLC to each of the two or more sPLCs; and
modifying an amount of performic acid produced by at least one of the two or more reactor units based on the second instruction.

21. The method of claim 20, wherein the modifying of the amount of performic acid produced comprises:
modifying, using two or more hydrogen peroxide pumps, a flow rate of hydrogen peroxide from the first source to at least one of the two or more reactor units; and
modifying, using two or more acid pumps, a flow rate of the one or more acids from the second source to at least one of the two or more reactor units.

22. The method of claim 21, wherein the modifying of the amount of performic acid produced by at least one of the two or more reactor units further comprises:
sending a third instruction from each of the two or more sPLCs to at least one of the two or more hydrogen peroxide pumps and to at least one of the two or more acid pumps in response to the second instruction from the mPLC.

23. The method of claim 20, wherein the modifying of the amount of performic acid produced comprises:
sending a signal to a coil valve to switch from a first coil having a first volume to a second coil having a second volume, thereby changing a residence time of precursors in the reactor unit, and a concentration of performic acid produced.

24. The method of claim 20, further comprising:
sending the status of each of the two or more reactor units through a modem to a cloud-based software platform,
wherein the cloud-based software platform facilitates (i) quality control, (ii) maintenance of the two or more reactor units, or (iii) a combination thereof in the event of a service need.

25. The method of claim 20, wherein modifying of the amount of performic acid produced by at least one of the two or more reactor units comprises increasing production of performic acid in a standby reactor unit from zero to the modified fraction of the desired level of performic acid.

26. The method of claim 20, wherein the modifying of the amount of performic acid produced by at least one of the two or more reactor units comprises modifying the production of performic acid in the two or more reactor units from an initial fraction to the modified fraction of the desired level of performic acid.

27. The method of claim 20, further comprising:
accepting, at a product outlet, a product comprising performic acid from each of the two or more reactor units.

28. The method of claim 20, wherein the disruptive event detected by the two or more sPLCs comprises (i) an unplanned failure of at least one of the two or more reactor units, (ii) a planned period of maintenance, (iii) a demand for an increased flow rate of performic acid, (iv) a demand for an increased concentration of performic acid, (v) a demand for a decreased flow rate of performic acid, (vi) a demand for a decreased concentration of performic acid, or (vii) a combination thereof.

29. A system for producing performic acid, the system comprising:
at least one reactor unit, wherein the at least one reactor unit comprises a water bath and two or more coils disposed in the water bath;
at least one servient programmable logic controller (sPLC), wherein the at least one sPLC is in communication with the at least one reactor unit;
a control panel comprising a master programmable logic controller (mPLC) in communication with the at least one sPLC; and
an automation unit having a user interface, wherein the automation unit is in communication with the mPLC.

30. The system of claim 29, wherein (i) the mPLC, (ii) the at least one sPLC, and (iii) the at least one reactor unit, are configured to maintain a desired level of performic acid production upon and/or after the occurrence of a disruptive event.

31. The system of claim 30, wherein:
the mPLC is configured to receive from the automation unit a first instruction comprising the desired level of performic acid production,
the mPLC is configured to receive a status of the at least one reactor unit from the at least one sPLC,
the mPLC is configured to send a second instruction, based on the desired level of performic acid production and the status of the at least one reactor unit, to the at least one sPLC upon and/or after the occurrence of the disruptive event, the second instruction comprising a modified fraction of the desired level of performic acid production, and
the at least one sPLC is configured to modify, based on the second instruction, an amount of performic acid produced by the two or more coils in the at least one reactor unit, such that a combined performic acid production of the two or more coils equals the desired level of performic acid production.

32. The system of claim 29, wherein the first coil has a first volume configured to produce a first concentration of performic acid, and the second coil has a second volume different than the first volume configured to produce a second concentration of performic acid.

33. A method of producing performic acid, the method comprising:
providing the system of claim 29;
sending a first instruction from the automation unit to the master programmable logic controller (mPLC);
supplying (i) hydrogen peroxide from a first source, and (ii) one or more acids from a second source to the at least one reactor unit;
sending a status of the at least one reactor unit from each of the at least one servient programmable logic controllers (sPLCs) to the mPLC;
sending a second instruction from the mPLC to each of the at least one sPLCs; and
modifying an amount of performic acid produced by each of the two or more coils based on the second instruction.

34. The method of claim 33, wherein the modifying of the amount of performic acid produced comprises:
modifying, using one or more hydrogen peroxide pumps, a flow rate of hydrogen peroxide from the first source to at least one of the two or more coils; and
modifying, using one or more acid pumps, a flow rate of the one or more acids from the second source to at least one of the two or more coils.

35. The method of claim 34, wherein the modifying of the amount of performic acid produced by at least one of the two or more coils further comprises:
sending a third instruction from each of the one or more sPLCs to at least one of the two or more hydrogen peroxide pumps and to at least one of the two or more acid pumps in response to the second instruction from the mPLC.

36. The method of claim 33, wherein the modifying of the amount of performic acid produced comprises:
sending a signal to a coil valve to switch from a first coil having a first volume to a second coil having a second volume, thereby changing a residence time of precursors in the rector unit, and a concentration of performic acid produced.

37. The method of claim 33, wherein the second instruction corresponds to a desired level of performic acid production in each of the two or more coils.

38. The method of claim 33, wherein the second instruction is generated by the at least one sPLC in response to detecting a disruptive event comprising (i) a demand for an increased flow rate of performic acid, (ii) a demand for an increased concentration of performic acid, (iii) a demand for a decreased flow rate of performic acid, (iv) a demand for a decreased concentration of performic acid, or (v) a combination thereof.

* * * * *